United States Patent [19]
Hikosaka et al.

[11] Patent Number: 6,004,514
[45] Date of Patent: Dec. 21, 1999

[54] PROCESS GAS CHROMATOGRAPHIC SYSTEM

[75] Inventors: Masatoshi Hikosaka; Hiroyuki Mutou, both of Toyko, Japan

[73] Assignee: Yamatake Corporation, Tokyo, Japan

[21] Appl. No.: 08/116,581

[22] Filed: Sep. 7, 1993

Related U.S. Application Data

[63] Continuation of application No. 07/832,915, Feb. 10, 1992, abandoned.

[30] Foreign Application Priority Data

Feb. 15, 1991 [JP] Japan ................................. 3-042220
Feb. 15, 1991 [JP] Japan ................................. 3-042221

[51] Int. Cl.$^6$ ............................................. G01N 30/02
[52] U.S. Cl. ........................... 422/89; 72/23.42; 96/104; 96/106; 422/70
[58] Field of Search ............... 422/70, 89; 210/656, 210/659, 198.2; 73/61.52, 61.53, 61.56, 23.35, 23.39, 23.24; 96/104, 106

[56] References Cited

U.S. PATENT DOCUMENTS

| | | | |
|---|---|---|---|
| 2,981,092 | 4/1961 | Marks | 73/23.42 |
| 3,069,894 | 12/1962 | Claudy | 73/23.42 |
| 3,070,989 | 1/1963 | Dueker et al. | 73/23.35 |
| 3,119,252 | 1/1964 | Nerheim . | |
| 3,139,755 | 7/1964 | Reineche et al. . | |
| 3,164,005 | 1/1965 | Burnell et al. | 73/23.22 |
| 3,199,274 | 8/1965 | Norem et al. | 73/23.42 |
| 3,205,701 | 9/1965 | Szonntagh | 73/23.35 |
| 3,276,243 | 10/1966 | Karas . | |
| 3,429,176 | 2/1969 | Topham | 73/23.35 |
| 3,858,435 | 1/1975 | Stevens | 422/89 |
| 3,897,211 | 7/1975 | Ririe, Jr. | 422/89 |
| 3,910,765 | 10/1975 | Tinkelpaugh et al. . | |
| 4,367,645 | 1/1983 | Froment | 73/23.42 |
| 4,474,889 | 10/1984 | Terry et al. | 422/89 |
| 4,854,952 | 8/1989 | Stephen | 72/23.35 |
| 5,114,439 | 5/1992 | Yost . | |
| 5,135,549 | 8/1992 | Phillips et al. . | |

FOREIGN PATENT DOCUMENTS

| | | |
|---|---|---|
| 430278 | 8/1967 | France . |
| 430278 | 2/1967 | Switzerland . |
| 9006507 | 6/1990 | WIPO . |

OTHER PUBLICATIONS

Advances in Instrumentation, vol. 40, Pt. 2, Villalobos et al, "Process Gas Chromatography", pp. 1435–1461.

*Primary Examiner*—Jan Ludlow
*Attorney, Agent, or Firm*—Lane Aitken & McCann

[57] ABSTRACT

A gas chromatographic system for analyzing gas components includes an analyzer, a constant temperature oven, an analyzer case, an indicator, an integrated sample conditioner, and a coupler. The analyzer includes a sample valve having a detector and a heater built therein and first and second columns wound around the periphery of the sample valve. The constant temperature oven accommodates the analyzer unit therein. The analyzer case accommodates the constant temperature oven. The indicator is protruded from the analyzer case to display analysis processes and results. The integrated sample conditioner provides an optimal condition for analysis. The coupler couples the analyzer unit with the sample conditioner so as to supply a sample gas and one of a carrier gas and a reference gas from the sample conditioner to the analyzer unit.

8 Claims, 7 Drawing Sheets

PROCESS GAS CHROMATOGRAPHIC SYSTEM

This is a Continuation of application Ser. No. 07/832,915 filed Feb. 10, 1992 now abandoned.

BACKGROUND OF THE INVENTION

The present invention relates to a process gas chromatographic system for analyzing a gas of interest by utilizing the difference in absorption between the gas and a filler filled in a column as a stationary phase.

Figure 9:
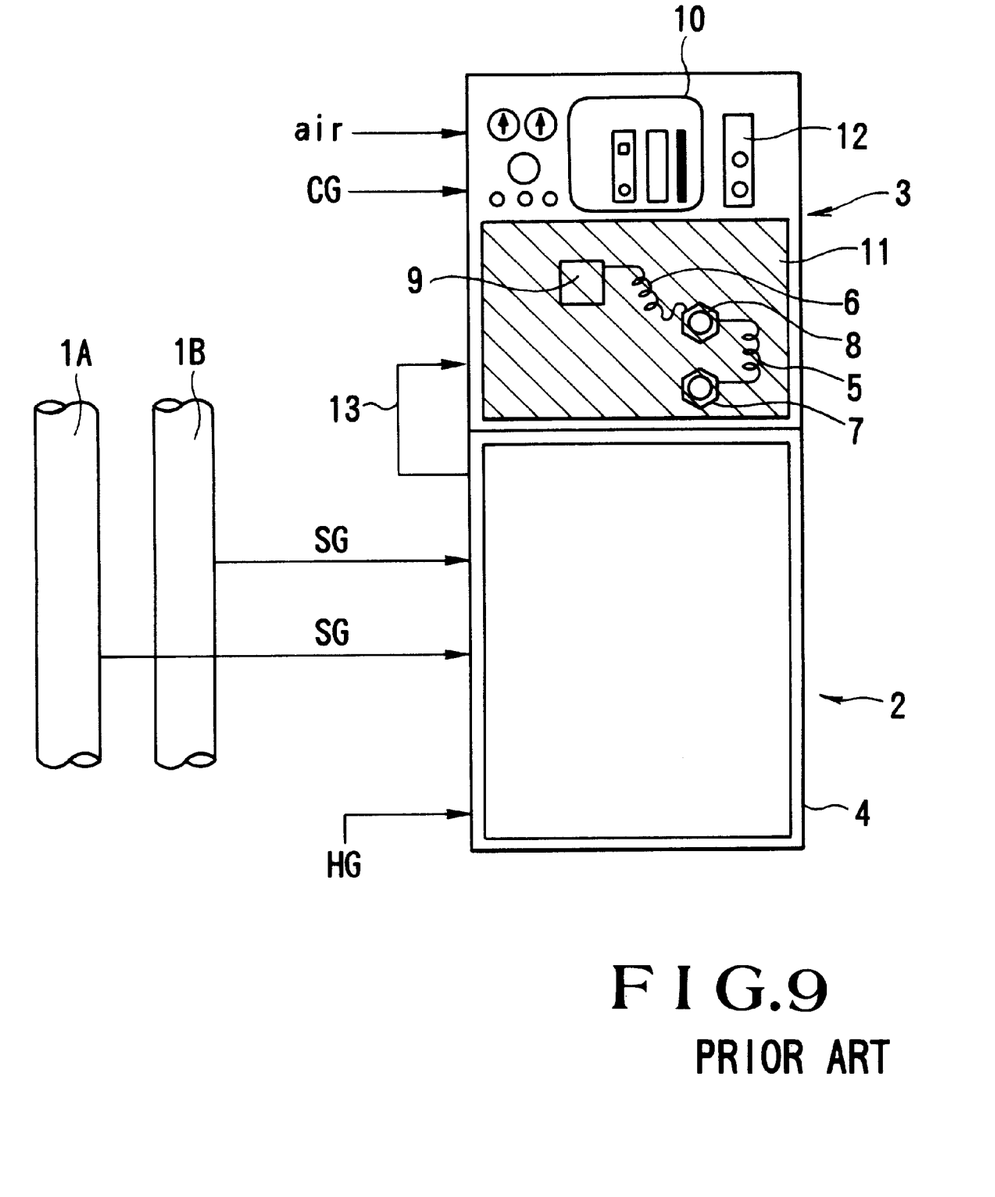
FIG. 9 is a front view of a conventional gas chromatographic system.

In industrial processes such as a petrochemical process and an iron and steel production process, a process gas chromatographic system for analyzing components of process gases is employed to provide a sample gas extracted from a process line with an optimal condition required for analysis by means of a sample conditioner unit, supply this sample gas to an analyzer unit to separate the same into respective gas components for detection, and monitor process steps and perform various control operations based on the analysis results. FIG. 9 shows a conventional gas chromatographic system of this type. Reference numerals 1A and 1B denote process lines; 2, a sample conditioner unit; and 3, an analyzer unit. The process lines 1A and 1B, the sample conditioner unit 2, and the analyzer unit 3 constitute the gas chromatographic system. The sample conditioner unit 2 includes a vaporizer (not shown) for perfectly vaporizing heavy components of a sample gas SG to prevent its condensation, a filter (not shown) for removing dust from the sample gas SG, a rotor meter (not shown) for measuring the flow rates of the sample gas SG and a reference gas HG, needle valves (not shown) for adjusting the flow rates of the reference gas HG and the sample gas SG, and a selector switch (not shown) for selecting an appropriate flow path. These components in the sample conditioner unit 2 are built in a housing 4 and are connected to each other through piping. The analyzer unit 3 includes first and second series-connected columns 5 and 6, a sample valve 7, a back-flush valve 8, a detector 9, a pressure reducing valve (not shown), an electric unit 10, a constant temperature oven 11, and a heater 12. The constant temperature oven 11 accommodates the first and second columns 5 and 6, the sample valve 7, the back-flush valve 8, the detector 9, and the like such that they are kept at an optimal temperature for separation analysis of the sample gas SG by circulating air heated by the heater 12. The first column 5 consists of a packed column which has an inner diameter of about 1 mm to 4 mm and a length of about 0.5 m to 3 m and in which a stationary phase is filled. The first column 5 can efficiently separate low-boiling point components containing small amounts of carbon (C) at high speed. The second column 6 consists of a capillary column which has an inner diameter of about 0.1 mm to 4 mm and a length of about 0.5 m to 3 m and which has the inner wall surface coated with a liquid phase. The second column 6 cannot easily separate low-boiling point components containing small amounts of carbon but can efficiently separate high-boiling point components having large amounts of carbon at high speed. In an actual analysis, heavy components having large amounts of carbon (i.e., high-boiling point components) in the sample gas SG are discharged by the back-flush valve 8 and are not subjected to measurement to shorten the analysis cycle and protect the column from deterioration. The low-boiling point components having small amounts of carbon alone are separated by the first column 5 at high speed. When a range of gas components having large amounts of carbon is to be measured, the second column 6 separates gas components (light components) having small amounts of carbon within this range. The gas components separated by the first and second columns 5 and 6 are converted into electrical signals by the detector 9. These electrical signals are proportional to the concentrations of the respective gas components.

In the conventional gas chromatographic system having the above structure, however, the temperature distribution in the constant temperature oven 11 cannot be made perfectly uniform due to the number of spray ports of the sample gas SG and a carrier gas CG and the layout of components of the system. In addition, variations in temperature also occur. For these reasons, the components such as the columns 5 and 6 cannot be maintained under optimal temperature conditions, whereby the detected concentrations of components do not often coincide with the sample concentrations, which results in difficulties in achieving accurate measurements. For example, with the sample gas SG susceptible to liquefaction, the sample valve 7 and the back-flush valve 8 are preferably maintained at high temperatures, and the second column 6 is preferably free from variations in temperature so as to improve the separation performance.

In the conventional apparatus, a sample inlet portion between the sample conditioner unit 2 and the analyzer unit 3 is connected by a sample pipe 13. To prevent a sample gas from being cooled down during the transportation through the sample pipe 13, the sample pipe 13 is double structured and heated with steam or the like. For this reason, the piping structure is complicated, and a large number of parts are required. If the sample conditioner unit 2 is placed close to the analyzer unit 3, a piping operation becomes difficult. On the contrary, the sample conditioner unit 2 placed far from the analyzer unit 3 will cause a large temperature drop of the sample gas, which results in requiring more energy to maintain a constant temperature.

The electric unit 10 including an amplifier and a temperature controller, since located generally above the thermostat together with the heater 12, is adversely affected by heat from the constant temperature oven 11 and the heater 12, thus degrading reliability of the apparatus. Further, the structure, in which the sample valve 7, the first and second columns 5 and 6, the detector 9, and the like are connected to each other through piping and couplings inside the constant temperature oven 11, may cause problems such as a difficult maintenance operation of these components.

SUMMARY OF THE INVENTION

It is an object of the present invention to provide a gas chromatographic system capable of preventing temperature fluctuations and maintaining a sample gas at a constant temperature.

It is another object of the present invention to provide a compact gas chromatographic system which can facilitate maintenance.

It is still another object of the present invention to provide a gas chromatographic system capable of reducing thermal influences of a heater and a constant temperature oven on electrical parts such as an amplifier and a temperature controller.

In order to achieve the above objects of the present invention, there is provided a gas chromatographic system for analyzing gas components comprising an analyzer unit including a sample valve having a detector and a heater built therein, and first and second columns wound around the periphery of the sample valve, a constant temperature oven in which the analyzer unit is accommodated, an analyzer case for accommodating the constant temperature oven, indicator means protruded from the analyzer case for displaying analysis processes and results, integrated sample conditioner means for providing an optimal condition for analysis, and coupler means for coupling the analyzer unit with the sample conditioner means so as to supply a sample gas and one of a carrier gas and a reference gas from the sample conditioner means to the analyzer unit.

DETAILED DESCRIPTION OF THE PREFERRED EMBODIMENT

A preferred embodiment of the present invention will be described with reference to the accompanying drawings.

Figure 1:
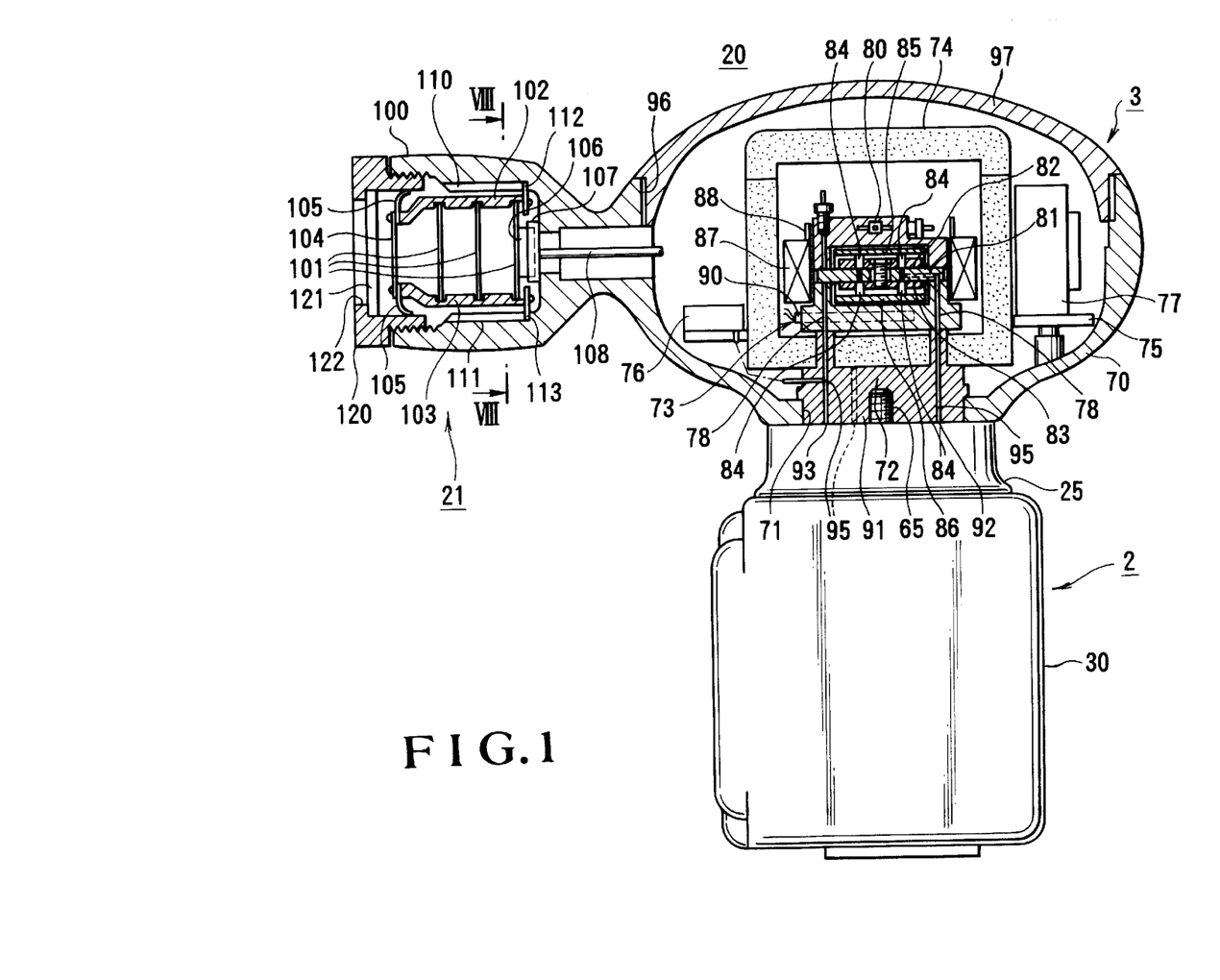
FIG. 1 is a sectional view showing a gas chromatographic system according to an embodiment of the present invention.
Figure 2:
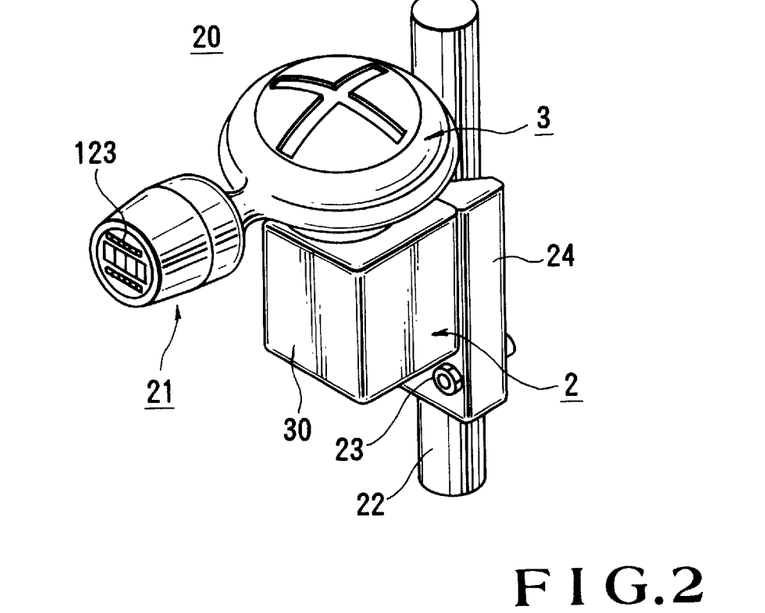
FIG. 2 is a perspective view showing that the gas chromatographic system shown in FIG. 1 is mounted on a stanchion.

Referring to FIGS. 1 and 2, a gas chromatographic system 20 comprises a sample conditioner unit 2, an analyzer unit 3 arranged above the sample conditioner unit 2, and an electric unit 21 connected to the front surface of the analyzer unit 3. The gas chromatographic system 20 is fixed on a stanchion 22 through a bracket 24 by a plurality of bolts 23.

The structure of the sample conditioner unit 2 will be described in detail with reference to FIGS. 3 to 6. The sample conditioner unit 2 comprises a box-like housing 30 having an upper central open portion. A housing block 31 made of a metal such as stainless steel is accommodated in the box-like housing 30.

Figure 3:
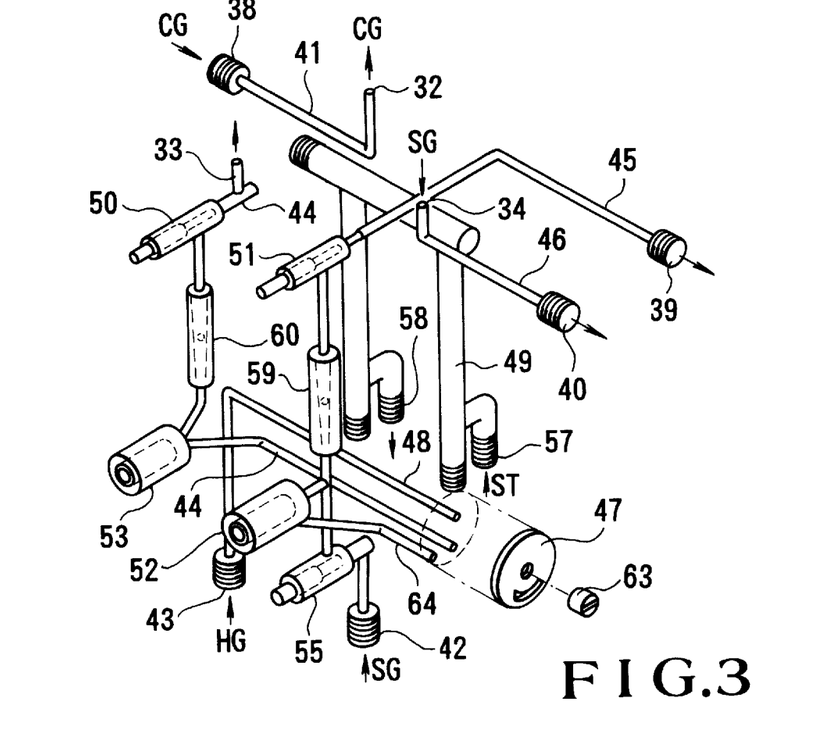
FIG. 3 is a perspective view showing an internal structure of a sample conditioner unit.
Figure 4:
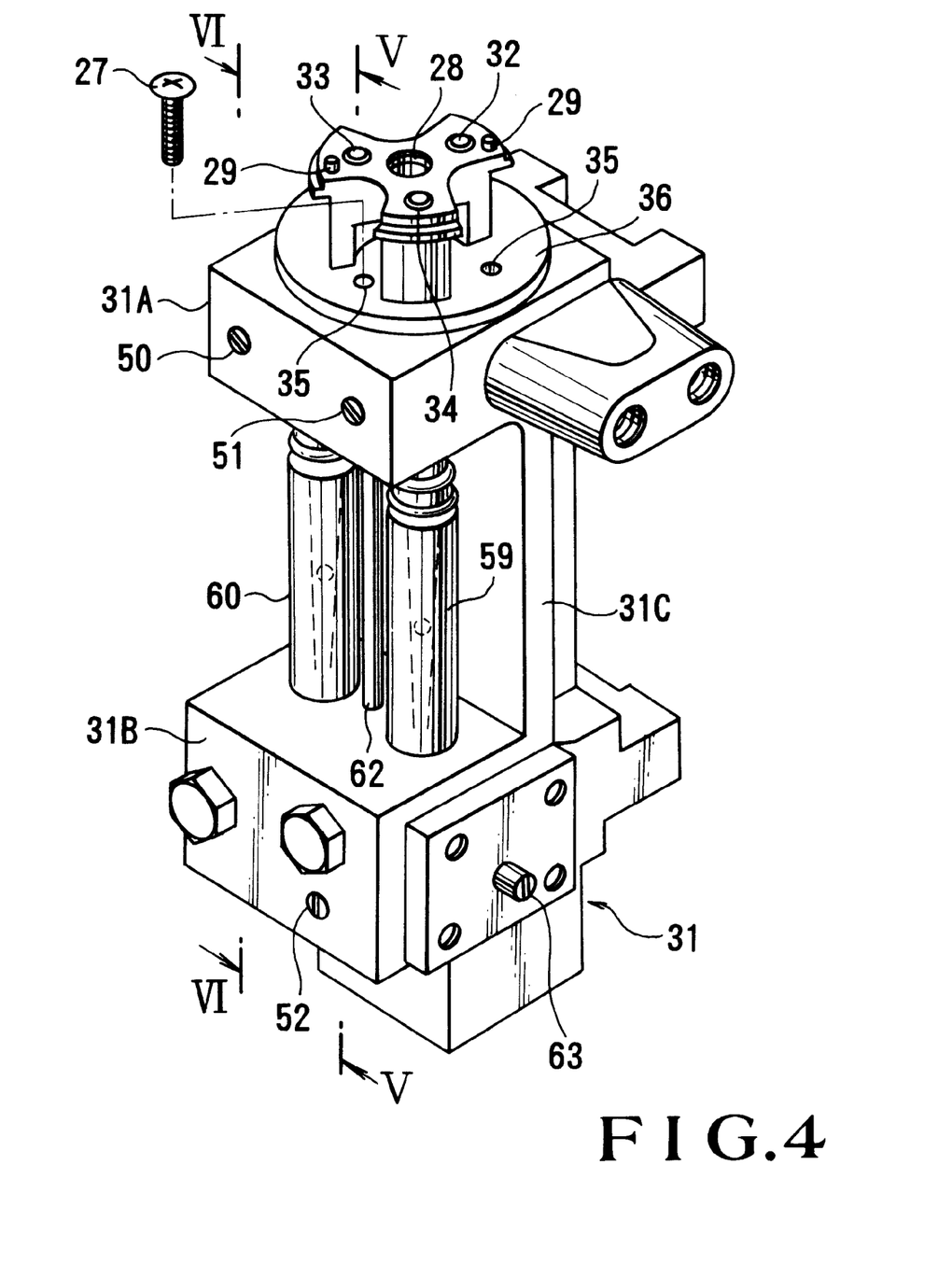
FIG. 4 is a perspective view showing the appearance of a housing block.
Figure 5:
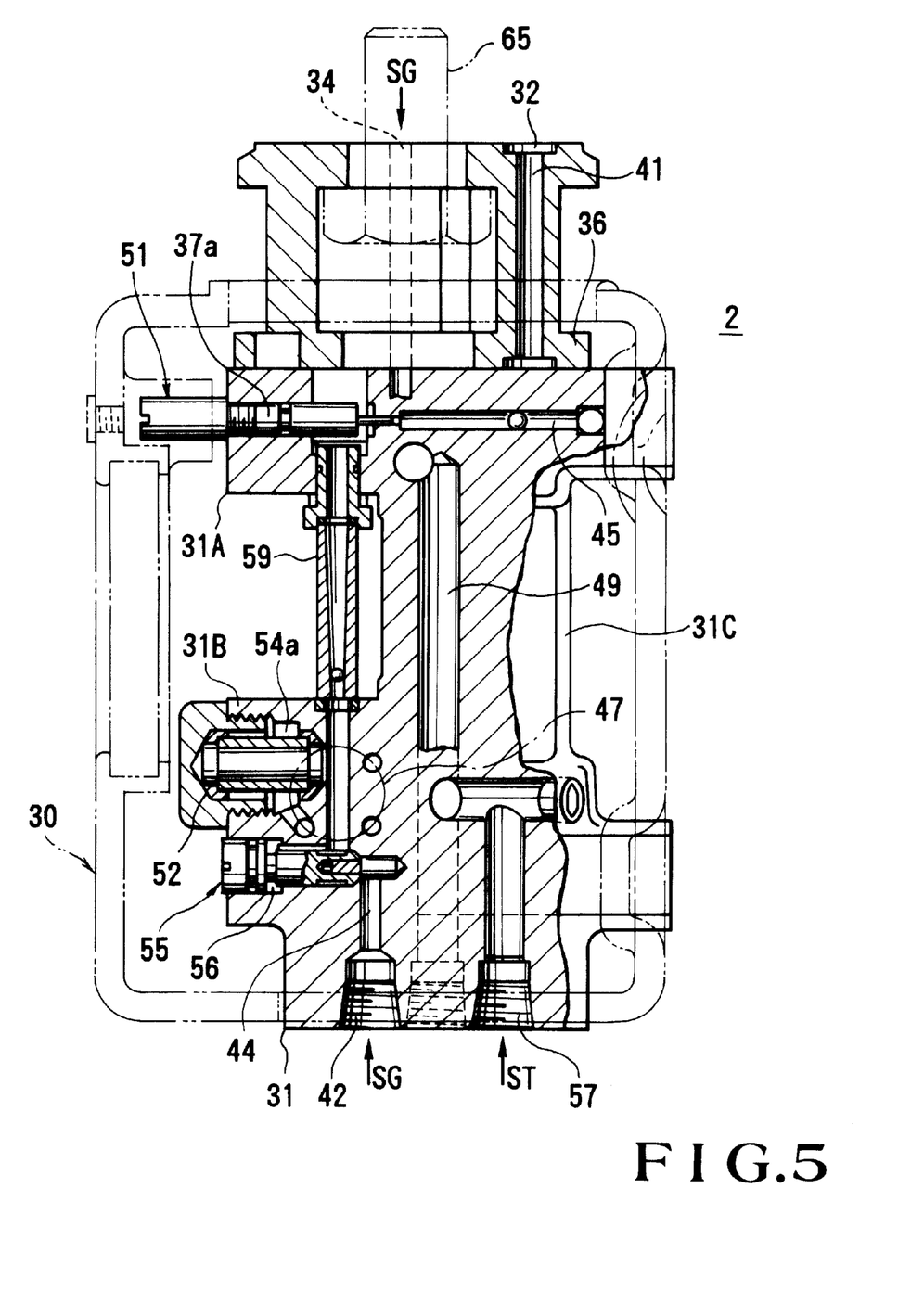
FIG. 5 is a sectional view of the housing block taken along the line V—V of FIG. 4.
Figure 6:
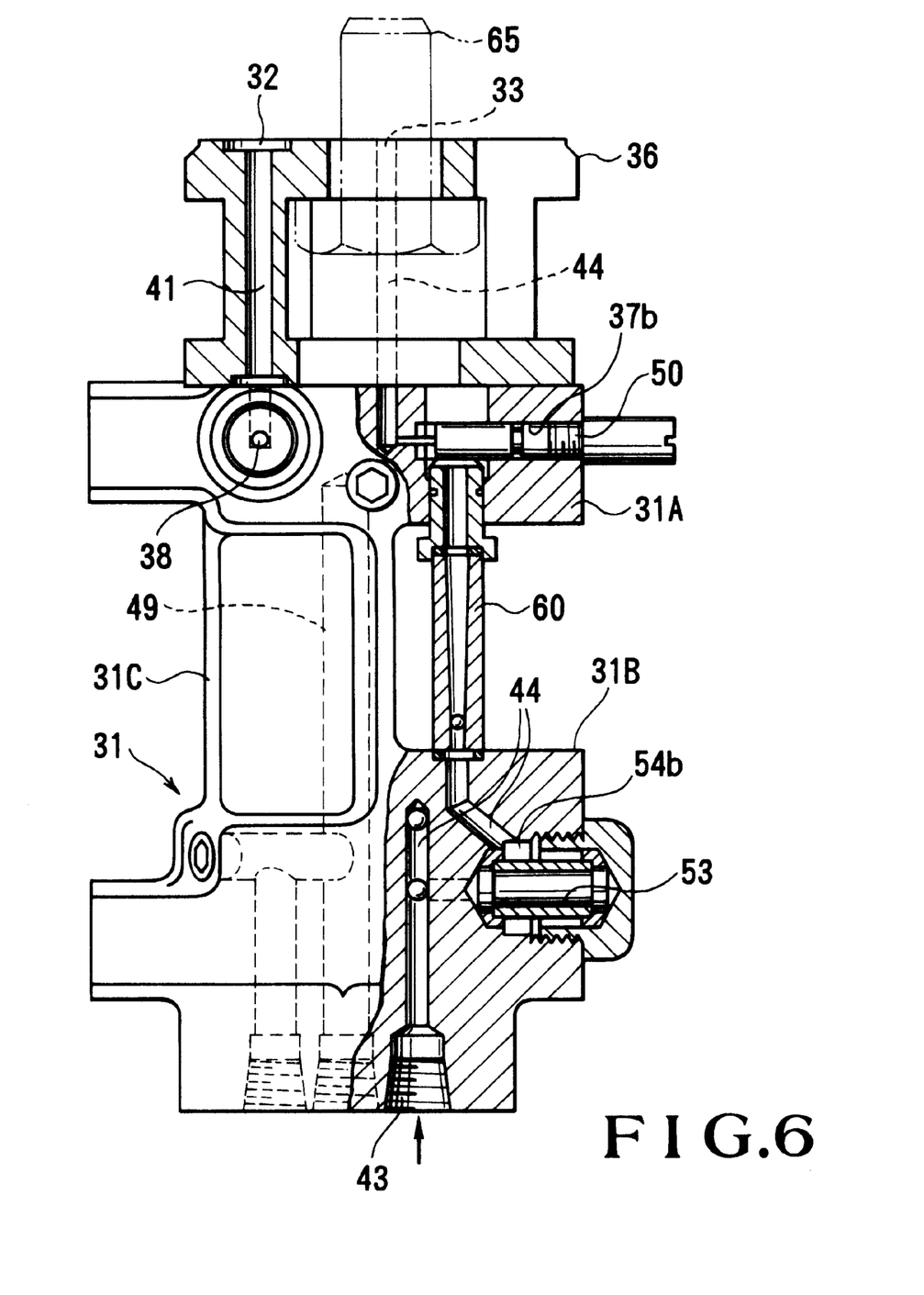
FIG. 6 is a sectional view of the housing block taken along the line VI—VI of FIG. 4.

The housing block 31 comprises vertically opposed, substantially horizontal upper and lower blocks 31A and 31B and a substantially vertical connecting portion 31C for connecting the upper and lower blocks 31A and 31B. A small block 36 having a carrier gas outlet port 32, a sample/reference gas outlet port 33, a sample gas inlet port 34, and a plurality of screw holes 35 is fixed on the upper surface of the upper block 31A by set screws 27. The small block 36 is covered with a cover 25 (FIG. 1). Two needle valve adjusting holes 37a and 37b are formed in the front surface of the upper block 31A. A carrier gas supply port 38 is formed in the left side surface of the upper block 31A. A bypass vent port 39 and a sample vent port 40 are formed in the right side surface of the upper block 31A. As shown in FIG. 3, a carrier gas flow path 41 communicating with the carrier gas outlet port 32 and the carrier gas supply port 38, a sample/reference gas flow path 44 for connecting the sample/reference gas outlet port 33 and a sample gas supply port 42 or a reference gas supply port 43, a bypass vent flow path 45 for connecting the bypass vent port 39 and an intermediate portion of the sample/reference gas, flow path 44, a sample vent flow path 46 for connecting the sample gas inlet port 34 and the sample vent port 40, a reference gas flow path 48 for connecting the reference gas supply port 43 and a selector switch 47, and a steam flow path 49 are formed inside the housing block 31. Referring to FIG. 4, reference numeral 28 denotes a bolt mounting hole for receiving from below a bolt 65 for fixing a manifold 72 (to be described later). Reference numerals 29 denote positioning pins for positioning the manifold 72.

Needle valves 50 and 51 are arranged midway along the sample/reference gas flow path 44 and the bypass vent flow path 45, respectively. The needle valves 50 and 51 are inserted into the needle valve adjusting holes 37a and 37b, respectively, and can be externally adjusted. A carrier gas CG is supplied to the carrier gas supply port 38 and is sent to the analyzer unit 3 through the carrier gas flow path 41 and the carrier gas outlet port 32. A sample gas SG after being separated and analyzed by the analyzer unit 3 is supplied to the sample gas inlet port 34 and is discharged from the sample vent port 40 through the sample vent flow path 46.

Two filter mounting holes 54a and 54b for respectively mounting filters 52 and 53, and a vaporizer mounting hole 56 for mounting a vaporizer 55 are formed in the front surface of the lower block 31B. The sample gas supply port 42, the reference gas supply port 43, a steam inlet 57, and a steam outlet 58 are formed in the lower surface of the lower block 31B. In addition to the filters 52 and 53 and the vaporizer 55, the selector switch 47 is incorporated inside the lower block 31B. The needle valve 50, the filters 52 and 53, the vaporizer 55, the selector switch 47, and a second rotometer 60 are incorporated midway along the sample/reference gas flow path 44. In addition to the needle valve 51, a first rotometer 59 is incorporated in the bypass vent flow path 45. The vaporizer 55 is arranged in a flow path between the sample gas supply port 42 and the filter 52. A reference gas HG is supplied to the reference gas supply port 43.

Each of the first and second rotometers 59 and 60 comprises a tapered pipe and a float. The first rotometer 59 measures the bypass flow rate of the sample gas SG, and the second rotor meter 60 measures the flow rate of the gas supplied to the analyzer unit 3. The first and second rotometers 59 and 60 are arranged between the upper and lower blocks 31A and 31B so that their upper and lower ends are detachable from the upper and lower blocks 31A and 31B. A thermometer 62 (FIG. 4) for measuring the temperature of the housing block 31 is arranged between the first and second rotometers 59 and 60 and hence between the upper and lower blocks 31A and 31B. More specifically, the first rotometers 59 is arranged between the filter 52 and the needle valve 51, and the second rotometer 60 is arranged between the filter 53 and the needle valve 50.

The selector switch 47 is switched upon rotation of a selection knob 63 manually or by a driving means such as a motor driven in response to a signal from a controller. The selection knob 63 is arranged on the right side surface of the lower block 31B. In a calibration mode using the reference gas, the selector switch 47 connects the sample reference gas flow path 44 to the reference gas flow path 48 to close a flow path 64 between the sample gas supply port 42 and the selector switch 47. In the calibration mode using the reference gas, the sample gas SG supplied from the sample gas supply port 42 is discharged from the bypass vent port 39 through the vaporizer 55, the first rotometer 59, the needle valve 51, and the bypass vent flow path 45. The reference gas HG supplied from the reference gas supply port 43 is supplied to the analyzer unit 3 through the selector switch 47, the filter 53, the reference gas flow path 44, the second rotometer 60, the needle valve 50, and the reference gas outlet port 33. At this time, the flow path 64 is kept closed by the selector switch 47.

In a measurement mode (during supply of the sample gas), the sample gas SG in place of the reference gas HG is supplied from the sample gas supply port 42 to the analyzer unit 3 through the vaporizer 55, the filter 52, the selector switch 47, the filter 53, the second rotometer 60, the needle valve 50, and the sample gas outlet port 33. When the sample gas SG is prepared, the selector switch 47 is switched to the calibration mode using the reference gas HG. Therefore, supply of the reference gas HG is resumed.

The arrangements of the vaporizer 55, the filters 52 and 53, the rotometers 59 and 60, and the selector switch 47 are the same as those of the conventional parts, and a detailed description thereof will be omitted.

Part of the steam flow path 49 is formed inside the connecting portion 31C for connecting the upper and lower blocks 31A and 31B. Steam ST is supplied to this part so as to utilize the housing block 31 as a heat exchanger, thereby heating the sample gas SG to a predetermined temperature (about 120° C. to 150° C.). The steam ST has a temperature of about 150° C. and a pressure of 10 kgf/cm$^2$ or less.

The detailed structure of the analyzer unit 3 will be described with reference to FIGS. 1 and 7. The analyzer unit 3 comprises an aluminum die cast analyzer case 70 consisting of an ellipsoidal body and arranged on the small block 36 of the sample conditioner unit 2. The manifold 72 is positioned on a lower surface opening portion 71 of the analyzer case 70 by the pins 29 (FIG. 4) formed on the small block 36 of the housing block 31 and is fixed by the bolt 65 from the lower side of the small block 36. A sample valve 73 and a constant temperature oven 74 which surrounds the sample valve 73 are formed on the upper surface of the manifold 72. An analyzer board 75 mounted with electric parts, a pressure reducing valve 76 for reducing the pressure of the carrier gas CG to a predetermined pressure, a transformer 77, and the like are arranged around the constant temperature oven 74 on the inner bottom portion of the case.

The sample valve 73 switches a fluid flow path 78 formed inside the valve 73. In the measurement mode, the sample valve 73 supplies the sample gas SG to a detector 80. In a non-measurement mode or a back-flush mode, the sample valve 73 supplies the carrier gas CG to the detector 80. The sample valve 73 comprises, for example, a known pneumatic diaphragm valve. More specifically, the sample valve 73 comprises a center plate 81, a plurality of plungers 84 respectively facing the upper and lower surfaces of the center plate 81 through diaphragms 82 and 83, and upper and lower pistons 85 and 86 for alternately driving the upper and lower plungers 84. The diaphragms 82 and 83 are alternately elastically deformed by gas pressures of the sample gas SG and the carrier gas CG, and the upper and lower plungers 84 are moved by the pistons 85 and 86, thereby alternately urging the plungers 84 to the diaphragms 82 and 83 and hence alternately switching the flow path 78 between the upper and lower routes. First and second columns 87 and 88 for separating the sample gas SG into gas components are arranged around the sample valve 73 such that the second column 88 is located inside the first column 87. The first column 87 is a packed column as described above and the second column 88 is a capillary column. In the sample valve 73, there are built the detector 80 and a heater 90 for heating the first and second columns 87 and 88 to predetermined temperatures. The detector 80, the heater 90, and the columns 87 and 88 constitute a main portion of the analyzer unit 3.

Since the sample valve 73 itself is substantially the same as a conventional pneumatic diaphragm valve except that the detector 80 and the heater 90 are built therein, a detailed description thereof will be omitted.

Figure 7:
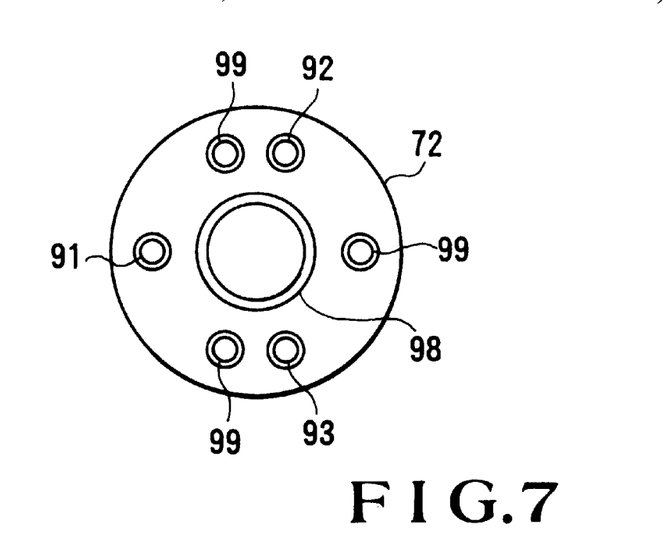
FIG. 7 is a bottom view of a manifold.

A carrier gas inlet port 91, a sample/reference gas inlet port 92, and a sample gas outlet port 93 are formed in the lower surface of the manifold 72, as shown in FIG. 7, such that they are respectively connected to the carrier gas outlet port 32, the sample/reference gas outlet port 33, and the sample gas inlet port 34 formed in the upper surface of the small block 36 (FIG. 4). The carrier gas inlet port 91, the sample/reference gas inlet port 92, and the sample gas outlet port 93 also communicate with the flow path 78 of the sample valve 73 through a flow path 95 (FIG. 1) formed inside the manifold 72.

In the analyzer case 70, a lid 97 is threadably engaged with an upper surface opening portion 96 and constitutes an explosion-proof case together with a circuit housing 100 (to be described later). Referring to FIG. 7, reference numeral 98 denotes a screw hole in which the bolt 65 is threadably engaged; and 99, screw holes for mounting a bracket used when the sample conditioner unit 3 is absent.

Figure 8:
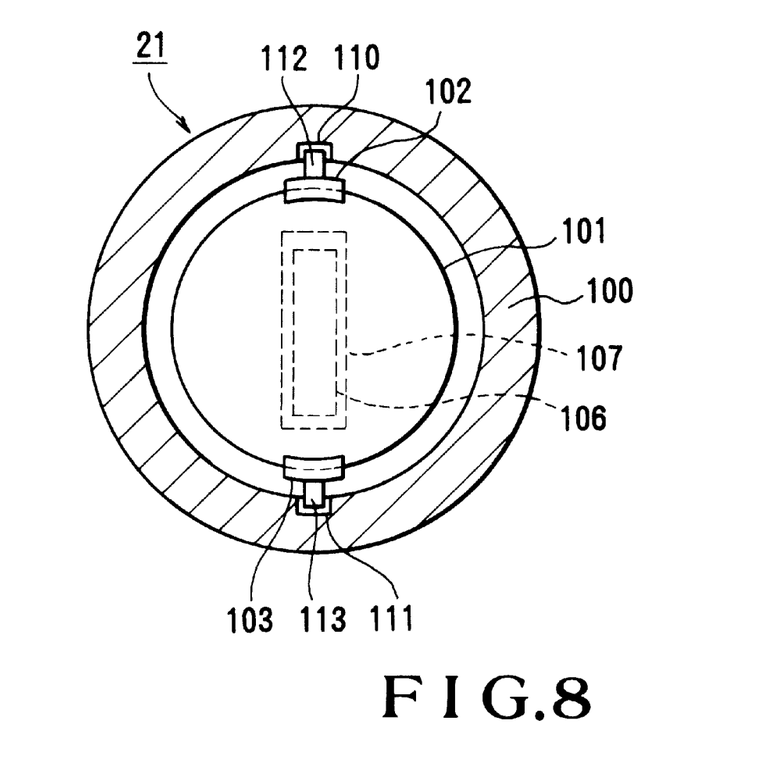
FIG. 8 is a sectional view of the gas chromatographic system taken along the line VIII—VIII of FIG. 1.

Referring to FIGS. 1 and 8, the electric unit 21 comprises the cylindrical housing 100 protruded from the front surface of the analyzer case 70. The circuit housing 100 comprises an aluminum die cast cylindrical body. The cylindrical housing 100 comprises printed circuit boards 101 mounted with electrical circuits (e.g., a constant temperature oven temperature control circuit) for driving and controlling the whole system 20, board fixing brackets 102 and 103 for holding the printed circuit boards 101, an indicator panel 104 for displaying analysis results, ground metal pieces 105, connectors 106 and 107, and the like. The case connector 107 is electrically connected to the analyzer unit 3 through a cord 108. Rotation preventive guide grooves 110 and 111 elongated in the axial direction are formed in the upper and lower portions of the inner circumferential surface of the housing 100 in correspondence with the board fixing brackets 102 and 103. Projections 112 and 113 which are inserted into the guide grooves 110 and 111 extend from the deep ends of the board fixing brackets 102 and 103.

Reference numeral 121 denotes a glass which closes an opening portion 122 of a lid 120; and 123, a nameplate.

In the electric unit 21 having the above arrangement, when the printed circuit boards 101 are to be mounted in the circuit housing 100, the projections 112 and 113 are respectively inserted into the rotation preventive guide grooves 110 and 111, and the printed circuit boards 101 are inserted into the circuit housing 100 together with the board fixing brackets 102 and 103. The board connector 106 is plugged in correspondence with the case connector 107 and is perfectly connected thereto, the projections 112 and 113 abut against the deep walls of the rotation preventive guide grooves 110 and 111, and further insertion is thus prevented. Then, by threadably engaging the lid 120 with the front side opening portion of the circuit housing 110, mounting of the printed circuit boards 101 and the lid 120 is completed. In this threadable engagement operation of the lid 120, the printed circuit boards 101 and the board fixing brackets 102 and 103 receive rotational moments caused by friction forces generated between the lid 120 and the ground metal pieces 105. However, since rotation of the brackets 102 and 103 is prevented by the rotation preventive guide grooves 110 and 111 and the projections 112 and 113, the printed circuit boards 101, the brackets 102 and 103, the connectors 106 and 107, and the like will not be twisted and are free from damage.

In the gas chromatographic system according to the present invention, as has been described above, since the fluid path ports of the analyzer unit and the sample conditioner unit are directly connected, and the sample piping can be eliminated, a decrease in temperature of the sample gas can be prevented. Assembly can be facilitated, and the number of parts such as couplings can be reduced. In addition, since the detector and the heater are incorporated in the sample valve, and the two columns are wound around the outer surface of the sample valve to obtain a unit assembly, piping between the valve and the detector can be eliminated, and maintenance operations can be facilitated. The printed circuit boards for the amplifier and the temperature controller, and the connectors are accommodated in the circuit housing so as to be separated from the constant temperature oven. Therefore, these components are not adversely affected by heat from the constant temperature oven, and reliability of the apparatus can be improved, thus providing many practical effects.

What is claimed is:

1. A gas chromatograph system for analyzing gas components comprising:
    (1) an analyzer unit having a plurality of fluid path ports and including:
        (a) a detector for electrically detecting concentrations of gas components;
        (b) a sample valve for supplying to said detector a sample gas in a measurement mode or a carrier gas in a non-measurement mode;
        (c) a heater for heating said sample valve and said detector, said heater and said detector being built into said sample valve;
        (d) first and second columns wound around the periphery of said sample valve, said first and second columns separating a sample gas heated by said heater into the gas components and supplying the separated gas components to said detector, said second column being located inwardly of said first column, properties of gas components separated by said second column being different from those of gas components separated by said first column;
        (e) a constant temperature oven in which said detector, said sample valve, said heater and said first and second columns are accommodated;
        (f) an analyzer case, comprising an ellipsoidal body, for accommodating said constant temperature oven, said analyzer case having an opening formed on a lower surface of the body;
    (2) an electric circuit unit including:
        (a) a cylindrical circuit housing protruded horizontally from said analyzer case and connected to said analyzer case; and
        (b) an electrical circuit unit, operatively coupled to said analyzer unit and accommodated in said cylindrical circuit housing, for driving and controlling analyses of the gas components by the system;
    (3) a sample conditioner unit, having a plurality of fluid path ports and arranged in tight contact with said opening in said analyzer case, for providing an optimal condition for the sample gas supplied to said sample valve in said analyzer unit;
    (4) a manifold, having a plurality of fluid path ports and formed so as to be fixedly fitted in said opening of said analyzer case, said manifold for fixedly coupling said constant temperature oven in said analyzer unit with said sample conditioner unit through said opening and directly supplying the sample gas and one of a carrier gas and a reference gas from said sample conditioner unit to said analyzer unit to prevent a decrease in temperature of the sample gas, and
    (5) indicator means connected to said electrical circuit and accommodated in said cylindrical housing for displaying at least analysis results said fluid path ports of said manifold including a carrier gas inlet port, another port for feeding one of a sample and reference gas, and a sample gas outlet port, said sample gas outlet port communicating with said sample valve in said analyzer unit, said constant temperature oven being disposed on an upper surface of said manifold;

said sample conditioner unit comprising a housing block fixed in tight contact with a lower surface of said manifold and having said plurality of fluid path ports of said sample conditioner unit therein, said plurality of fluid path ports of said sample conditioner unit including a carrier gas outlet port connected to the carrier gas inlet port of said manifold, another outlet port for supplying one of a sample and reference gas to said another inlet port of said manifold, and a sample gas vent port connected to the sample gas outlet port of said manifold;

said manifold adapted to be fitted in said analyzer case is fixed by a bolt positioned in said housing block so as to cause said gas outlet ports to communicate with said gas inlet ports;

said cylindrical circuit housing including a neck portion, having a predetermined diameter for preventing an influence due to heat conduction from said constant temperature oven, for connecting to said analyzer case.

2. A gas chromatographic system according to claim 1, wherein said analyzer case comprises an aluminum die cast body, and said circuit housing comprises an aluminum die cast cylindrical body.

3. A gas chromatographic system according to claim 1, wherein said second column efficiently separates high-boiling components having first predetermined amounts of carbon at a predetermined speed and is wound around said sample valve, and said first column efficiently separates low-boiling components having second predetermined amounts of carbon and is wound around said second column, said second predetermined amounts of carbon being smaller than said first predetermined amounts of carbon.

4. A gas chromatograph system according to claim 1, wherein said analyzer case and said cylindrical circuit housing constitute an explosion-proof case.

5. A gas chromatograph system according to claim 1, wherein said sample valve includes a fluid flow path therein and means for alternately switching the fluid flow path between said measurement mode and said non-measurement mode, said ellipsoidal body comprising an aluminum body and said circuit housing comprising an aluminum body.

6. An analyzer for gas chromatograph comprising:
    an analyzer case, comprising an ellipsoidal body, for accommodating a constant temperature oven, said analyzer case having an opening formed on a lower surface of the body;
    a manifold formed so as to be fixedly inserted into said opening, said manifold having a plurality of fluid path ports including a carrier gas inlet port, another inlet port for feeding one of a sample gas with an optimal condition and a reference gas, and an outlet port for removing said one of the sample gas and the reference gas;

said constant temperature oven being disposed on and fixed to said manifold;

a sample valve, disposed in said constant temperature oven, said sample valve having a heater and a detector built therein, said detector electrically detecting concentrations of gas components and said heater heating said sample valve;

first and second columns wound around said sample valve for separating a sample gas supplied by said sample valve into the gas components and supplying the separated gas components to said detector, said second column being located inwardly of said first column, properties of gas components separated by said second column being different from those of gas components separated by said first column;

a cylindrical housing protruded horizontally from said analyzer case and connected to said analyzer case through a neck portion having a predetermined diameter for preventing an influence due to heat conduction from said constant temperature oven;

an electrical circuit unit operatively coupled to said analyzer case and accommodated in said cylindrical housing for driving and controlling analyses of the gas components by said analyzer; and indicator means connected to said electrical circuit and accommodated in said cylindrical housing for displaying at least analysis results.

7. An analyzer according to claim 6, wherein said analyzer case and said cylindrical circuit housing constitute an explosion-proof case.

8. An analyzer according to claim 6, wherein said sample valve includes a fluid flow path therein and means for alternately switching the fluid flow path between first and second routes, said ellipsoidal body comprising an aluminum body and said circuit housing comprising an aluminum body.

* * * * *